United States Patent [19]

Harbuck

[11] 4,021,476

[45] May 3, 1977

[54] VINYL ACETATE POLYMERIZATION INHIBITORS

[75] Inventor: Linda Ann Harbuck, Charleston, W. Va.

[73] Assignee: Union Carbide Corporation, New York, N.Y.

[22] Filed: Dec. 29, 1975

[21] Appl. No.: 644,842

[52] U.S. Cl. .............................. 260/497 R; 203/8; 203/DIG. 10; 260/497 A; 260/488 H
[51] Int. Cl.² ..................... C07C 67/05; B01D 3/00
[58] Field of Search ....... 260/497 A, 497 R, 488 H; 203/DIG. 10, 8

[56] References Cited

UNITED STATES PATENTS 3,691,021  9/1972  Feldman ...................... 260/497 A

OTHER PUBLICATIONS

Bagdasar'ian, J. Poly. Sci. 52, pp. 31–38 (1961).

*Primary Examiner*—Lorraine A. Weinberger
*Assistant Examiner*—Michael Shippen
*Attorney, Agent, or Firm*—Bernard Francis Crowe

[57] ABSTRACT

The polymerization of vinyl acetate during distillation can be inhibited by 4-(2,6-dimethylheptyl) phenol and other liquid p-alkyl phenols.

3 Claims, No Drawings

VINYL ACETATE POLYMERIZATION INHIBITORS

BACKGROUND OF THE INVENTION

Vinyl acetate is produced commercially by the reaction of ethylene with molecular oxygen and acetic acid in the presence of a catalyst followed by the purification of the crude vinyl acetate so produced by distillation. Because vinyl acetate is a relatively reactive monomer, it is susceptible to polymerization by radical initiators that may be present either as impurities in raw materials, or in reaction products, or as monomer-derived radicals which are produced thermally during the distillation. Polymer formation in distillation equipment results in decreased yields of vinyl acetate as well as plugging and damaging of the equipment. These undesirable effects result in increased downtime for clean-up and repair of the equipment used.

A number of polymerization inhibitors have been used in the past to prevent this undesirable polymerization of vinyl acetate monomer. Among these are hydroquinone, benzoquinone, tertiary-butyl catechol, alphamethylstyrene, and the like. Major criteria for selecting a satisfactory polymerization inhibitor in vinyl acetate production include effectiveness in preventing polymer build-up, low cost of the inhibitor on an effectiveness basis, commercial availability, ease of handling, safety considerations, solubility of the inhibitor in vinyl acetate and the effect of minute inhibitor residues on waste water treatment systems. It is also desirable that the inhibitor have a significant vapor pressure at process distillation temperatures. Such volatility permits the inhibitor to protect all surfaces of the distillation vessel during the refining steps and especially above the point where the inhibitor solution is injected into the distillation columns. The area above the column feed points are particularly susceptible to plugging. It is further required that the inhibitor for this process contain only the elements carbon, hydrogen, and oxygen so that residual inhibitor contained in recycled acetic acid will not poison the vinyl acetate catalyst system nor contribute to reactor corrosion.

An inhibitor which fulfills most of the above enumerated criteria will often have some unique disadvantage that makes it less attractive for use in an actual commercial unit. An example of this is tertiary-butyl catechol which is ineffective as an inhibitor for vinyl acetate in a reducing atmosphere. This inhibitor requires the use of a stream of oxygen which must be run continuously through all the distillation columns to which this inhibitor is supplied. More frequently, inhibitor cost and commercial availability are key factors that influence its practical use.

SUMMARY OF THE INVENTION

Inhibitors which satisfy all the criteria above for the inhibition of polymerization of vinyl acetate monomer during distillation are the class of p-alkyl phenols having about 4 to about 18 carbon atoms in the alkyl group. The preferred p-alkyl phenol because of inhibition activity, cost, and availability is 4-(2,6-dimethylheptyl) phenol. Other p-alkyl phenols which can be used for the inhibition of vinyl acetate polymerization during distillation include: 4-tert-butyl phenol, 4-sec-butyl phenol, 4-n-pentyl phenol, 4-isopentyl phenyl, 4-hexyl phenol, 4-octyl phenol, 4-dodecyl phenol, 4-octadecyl phenol, and the like.

If an inhibitor is to be useful, it must result in an induction period during which there is no polymer formation in the monomer system. This induction period must be longer than the maximum length of time that can be envisioned for the contact time of a representative vinyl acetate molecule during each of the purification stages. This induction period will depend on inhibitor concentration and on the concentration of any initiator present. In order to evaluate a set of inhibitors, the respective induction periods under various inhibitor-initiator levels must be determined.

This evaluation of inhibitors requires some parameter that can be used to quantity the extent of polymerization of vinyl acetate. Quite handily the vinyl acetate system lends itself to monitoring viscosity versus time since the polymer, polyvinyl acetate, is very soluble in monomer in the range of commercial interest.

Under similar conditions, i.e., the same ratio of solvent to monomer and the same concentration of impurities, vinyl acetate will yield polymer of the same molecular weight distribution when the percent conversion to polyvinyl acetate is low (less than 10 percent). In this low range of polyvinyl acetate concentration with the crude vinyl acetate reaction product as solvent, viscosity vs. polymer concentration is linear. Thus viscosity versus time plots can be used as an indication of polyvinyl acetate content in a samle without concern for interference by variable molecular weight or branching effects. Oligomers do not contribute to a change in viscosity, while highly branched high molecular weight polyvinyl acetate will contribute markedly. These effects can be ignored if the molecular weight distribution of any polymer is constant for all samples.

In order to observe significant viscosity changes over reasonable lengths of laboratory operating time, dibenzoyl peroxide, a free radical polymerization initiator, was added to most samples. While the conditions induced by adding initiator are probably more severe than would be encountered in practice in a refining operation, they may exaggerate the effect of highly reactive, vinyl acetate-derived radicals that propagate rapidly to form polymer in the abovementioned process.

The change in viscosity with time was monitored initially for seven inhibitor candidates at different concentrations of inhibitor and initiator. Induction periods prior to polymer formation were estimated from plots of viscosity versus time data. For all cases the least polymer was found in the presence of high concentration of inhibitor (100 ppm) and in the absence of initiator; the most polymer was formed with low inhibitor (50 ppm) and high initiator (100 ppm). Nalene, a trademark of Tenneco Chemicals, for 2,6-dimethyl (2,3,6)-octatriene and alpha-methyl styrene showed zero induction periods ($t_i$) under all conditions investigated. Tert-butylcatechol, benzoquinone and Tenamene-4, a trademark of Tennessee Eastman Co. for N,N'-bis(1,4-dimethylpentyl)-p-phenylenediamine, showed intermediate induction periods greater than 24 hours at inhibitor:initiator ratios of 100 ppm: 0 ppm, 100 pm: 100 ppm, and 50 ppm: 0 ppm respectively. These three inhibitors had 0 induction periods at a 50 ppm: 100 ppm inhibitor:initiator ratio. Of the inhibitors compared, the nonyl phenol, 4-(2,6-dimethylheptyl) phenyl, had an induction period greater than 48 hours at inhibitor:initiator ratios of 100 ppm: 50 ppm and greater than 24 hours at 50 ppm: 0 ppm, 50 ppm: 100 ppm, and 100 ppm: 100 ppm. Hydroquinone shows induction periods similar to those of this p-nonyl phenol but hydroquinone is clearly inferior because of its low solubility in vinyl acetate, requiring the use of a co-solvent, and due to its solid state at normal temperatures. The p-nonyl phenol referred to above is highly soluble in vinyl acetate and is a liquid at normal temperatures.

Another advantage of p-nonyl phenol, in addition to its liquid state and miscibility in vinyl acetate, is its insolubility in ater. This affords ease in handling with no opportunity for this inhibitor to get into the waste streams. Hydroquinone is soluble in water and thus complicates waste water treatment. p-Nonyl phenol can also be effective above the point of injection into the distillation columns. Because it is a liquid, its vapor pressure at the unit operating temperatures enables it to protect the apparatus even on surfaces where there is no direct contact by the inhibitor stream.

Viscosities were measured using 5 cc. samples in a Cannon-Fenske viscometer. The viscosity measured in centipoises is the product of the efflux time in seconds X a calibration factor X a density factor.

The validity of the viscosity method to evaluate different vinyl acetate polymerization inhibitors was supported by a statistical analysis of the viscosity data obtained. An analysis of variance was done on the adjusted induction times for the inhibitors. Induction times were estimated conservatively from the viscosity versus time plots for each inhibitor under each set of conditions. The adjustment consists of subtracting the induction time for the control samples from the induction times of each inhibitor.

The invention is further described in the examples which follow. All parts and percentages are by weight unless otherwise specified.

EXAMPLE 1

Samples were prepared for polymerization inhibitor activity in nitrogen-purged, 4 ounce glass bottles which contained 100 ppm (by weight) of dibenzoyl peroxide and 50 ppm of each of the inhibitors tabulated below in a solution of simulated plant crude vinyl acetate of the following composition:

| COMPONENT | WEIGHT % |
| --- | --- |
| Acetic Acid | 74 |
| Vinyl Acetate | 20 |
| Water | 5 |
| Acetaldehyde | 0.2 |
| Acrolein | 0.3 |
| Ethyl Acetate | 0.3 |
| Ethylidene Diacetate | 0.2 |
| Ferric Acetate | trace |

The solutions wee tightly capped, warmed at 72° C. (boiling point of vinyl acetate at 760 mm) for 4 hours and quenched at 0° C. prior to opening. Sample viscosities were determined using the Cannon-Fenske viscometers in a 25° C. constant temperature bath. The same samples were then rewarmed for a total of 24 and 48 hours and the above process repeated. The Control sample A contained 100 ppm of dibenzoyl peroxide but no inhibitor. The viscosities observed were recorded in Table 1.

TABLE 1

| | VISCOSITIES OF SAMPLES IN CENTIPOISE | | | | | | | |
| --- | --- | --- | --- | --- | --- | --- | --- | --- |
| | INHIBITORS | | | | | | | |
| Time hours | None, Control A | t-Butyl Catechol | Hydro-quinone | Berzo-quinone | α-Methyl Styrene | Nalene | Tenamene 4 | Nonyl Phenol [1] |
| 4 | 1.273 | 1.273 | 1.325 | 1.279 | 1.260 | 1.282 | 1.267 | 1.260 |
| 24 | 3.086 | 2.511 | 1.852 | 2.361 | 3.191 | 3.034 | 2.380 | 1.332 |
| 48 | 5.459 | 4.360 | 3.762 | 4.000 | 4.723 | 4.896 | 4.299 | 3.352 |

[1] 4-(2,6-dimethylheptyl) phenol

EXAMPLE 2

Samples prepared as in Example 1 contained 100 ppm dibenzoyl peroxide and 100 ppm of the seven polymerization inhibitors in simulated crude vinyl acetate having the composition given in Example 1. The samples were warmed at 72° C., quenched at 0° C., and their viscosities measured at the same intervals as those disclosed in Example 1 affording the data shown in Table 2.

TABLE 2

| | VISCOSITIES OF SAMPLES IN CENTIPOISE | | | | | | | |
| --- | --- | --- | --- | --- | --- | --- | --- | --- |
| | INHIBITORS | | | | | | | |
| Time hours | None, Control B | t-Butyl Catechol | Hydro-quinone | Berzo-quinone | α-Methyl Styrene | Nalene | Tenamene 4 | Nonyl Phenol[1] |
| 4 | 1.257 | 1.340 | 1.281 | 1.267 | 1.289 | 1.311 | 1.265 | 1.260 |
| 24 | 3.381 | 1.438 | 1.345 | 1.336 | 2.425 | 2.444 | 1.413 | 1.817 |
| 48 | 5.278 | 3.661 | 2.849 | 2.682 | 4.838 | 4.043 | 3.154 | 3.059 |

[1] 4-(2,6-dimethylheptyl) phenol

EXAMPLE 3

Samples prepared as in Example 1 but containing no benzoyl peroxide and containing 100 ppm of the seven inhibitors in simulated crude vinyl acetate were evaluated. The samples were warmed at 72° C., quenched, and their viscosities measured at 4, 24 and 48 hours. The viscosity data obtained are contained in Table 3.

TABLE 3

| | VISCOSITIES OF SAMPLES IN CENTIPOISE | | | | | | | |
|---|---|---|---|---|---|---|---|---|
| | INHIBITORS | | | | | | | |
| Time hours | None, Control C | t-Butyl Catechol | Hydro- quinone | Benzo- quinone | α-Methyl Styrene | Nalene | Tenamene 4 | Nonyl Phenol[1] |
| 4 | 1.248 | 1.235 | 1.257 | 1.251 | 1.525 | 1.258 | 1.245 | 1.276 |
| 24 | 2.428 | 1.245 | 1.234 | 1.364 | 2.186 | 3.564 | 1.321 | 1.262 |
| 48 | 4.325 | 2.337 | 1.236 | 2.726 | 3.961 | 5.751 | 2.444 | 1.258 |

[1] 4-2,6-dimethylheptyl) phenol

EXAMPLE 4

Samples prepared as in Example 1 with 50 ppm of the seven polymerization inhibitors but containing no benzoyl peroxide in the simulated crude vinyl acetate were evaluated. The samples were warmed at 72° C., quenched, and their viscosities measured at 4, 24 and 48 hours. The data obtained are presented in Table 4.

TABLE 4

| | VISCOSITIES OF SAMPLES IN CENTIPOISE | | | | | | | |
|---|---|---|---|---|---|---|---|---|
| | INHIBITORS | | | | | | | |
| Time hours | None, Control D | t-Butyl Catechol | Hydro- quinone | Benzo- quinone | α-Methyl Styrene | Nalene | Tenamene 4 | Nonyl Phenol[1] |
| 4 | 1.220 | 1.231 | 1.226 | 1.383 | 1.226 | 1.286 | 1.290 | 1.250 |
| 24 | 1.978 | 1.246 | 1.243 | 1.524 | 2.151 | 2.595 | 1.694 | 1.251 |
| 48 | 3.993 | 4.489 | 2.845 | 3.761 | 4.304 | 5.137 | 3.643 | 3.459 |

[1] 4-(2,6-dimethylheptyl) phenol

EXAMPLE 5

The procedure described in Example 1 was followed for evaluating several p-alkyl phenols in comparison with 4-(2,6-dimethylheptyl) phenol, t-butyl catechol, and hydroquinone as inhibitors for the polymerization of the vinyl acetate. The crude vinyl acetate solution described in Example 1 was again used with 25 ppm of inhibitor and no benzoyl peroxide initiator. The samples were heated at 72° C., quenched, and their viscosities recorded at intervals. The data obtained together with that of a Control E where no inhibitor was used are recorded in Table 5.

TABLE 5

| | VISCOSITIES OF SAMPLES IN CENTIPOISE | | | | | | | |
|---|---|---|---|---|---|---|---|---|
| | INHIBITORS | | | | | | | |
| Time hours | None Control E | 4-t-Butyl Phenol | 4-sec-Butyl Phenol | 4-t-Butyl Catechol | Hydro- quinone | 4-Dodecyl Phenol | 4-n-Pentyl Phenol | 4-Nonyl Phenol[1] |
| 15 | 1.321 | 1.272 | 1.267 | 1.274 | 1.267 | 1.308 | 1.295 | 1.290 |
| 18 | 1.300 | 1.295 | 1.332 | 1.322 | 1.336 | 1.415 | 1.361 | 1.364 |
| 28 | 1.439 | 1.302 | 1.303 | 1.303 | 1.331 | 1.328 | 1.282 | 1.259 |
| 32 | 1.894 | 1.347 | 1.318 | 1.348 | 1.335 | 1.344 | 1.346 | 1.327 |
| 34 | 1.898 | 1.303 | 1.281 | 1.349 | 1.335 | 1.309 | 1.290 | 1.298 |
| 46.5 | 3.577 | 1.600 | 1.279 | 2.967 | 2.253 | 1.361 | 1.304 | 1.302 |
| 50.5 | 3.704 | 2.042 | 1.330 | 3.076 | 2.594 | 1.689 | 1.324 | 1.509 |
| 52.5 | 3.886 | 2.249 | 1.323 | 3.876 | 2.876 | 1.867 | 1.427 | 1.646 |
| 65 | 4.526 | 3.352 | 2.274 | 3.896 | 3.753 | 2.844 | 2.099 | 3.040 |

[1] 4-(2,6-dimethylheptyl) phenol

EXAMPLE 6

Example 5 was repeated with the exception that 100 ppm of benzoyl peroxide initiator was added to the samples in addition to the 25 ppm of inhibitor. The viscosity data are contained in Table 6.

TABLE 6

| | VISCOSITIES OF SAMPLES IN CENTIPOISE | | | | | | | |
|---|---|---|---|---|---|---|---|---|
| | INHIBITORS | | | | | | | |
| Time hours | None, Control F | 4-t-Butyl Phenol | 4-sec-Butyl Phenol | 4-t-Butyl Catechol | Hydro- quinone | 4-Dodecyl Phenol | 4-n-Pentyl Phenol | 4-Nonyl Phenol[1] |
| 16 | 1.388 | 1.332 | 1.387 | 1.288 | 1.290 | 1.293 | 1.320 | 1.312 |
| 20 | 1.355 | 1.301 | 1.301 | 1.334 | 1.286 | 1.331 | 1.302 | 1.281 |
| 25 | 1.426 | 1.305 | 1.305 | 1.354 | 1.352 | 1.279 | 1.306 | 1.335 |
| 37.5 | 3.166 | 1.706 | 1.350 | 2.437 | 1.652 | 1.681 | 1.390 | 2.571 |
| 40.5 | 3.566 | 1.770 | 1.690 | 2.826 | 1.956 | 2.042 | 1.537 | 2.668 |
| 44 | 3.778 | 2.282 | 2.109 | 3.179 | 2.362 | 2.565 | 1.970 | 3.022 |
| 56.5 | 4.559 | 3.635 | 3.423 | 4.131 | 3.689 | 3.918 | 3.149 | 4.013 |
| 58.5 | 4.616 | 4.158 | 3.442 | 4.340 | 3.605 | 3.711 | 3.321 | 4.210 |
| 75.5 | 5.437 | 4.325 | 4.335 | 5.284 | 4.902 | 4.839 | 4.597 | 4.962 |

[1] 4-(2,6-dimethylheptyl) phenol

EXAMPLE 7

Example 5 was repeated with the exception that no benzoyl peroxide initiator was used and 50 ppm of inhibitor was added to the samples. The viscosity data are contained in Table 7.

TABLE 7

VISCOSITIES OF SAMPLES IN CENTIPOISE
INHIBITORS

| Time hours | None, Control G | 4-t-Butyl Phenol | 4-sec-Butyl Phenol | 4-t-Butyl Catechol | Hydro-quinone | 4-Dodecyl Phenol | 4-n-Pentyl Phenol | 4-Nonyl Phenol[1] |
|---|---|---|---|---|---|---|---|---|
| 4 | 1.319 | 1.286 | 1.259 | 1.270 | 1.235 | 1.325 | 1.310 | 1.257 |
| 21.5 | 1.317 | 1.310 | 1.290 | 1.290 | 1.255 | 1.263 | 1.250 | 1.274 |
| 24.5 | 1.364 | 1.321 | 1.258 | 1.321 | 1.286 | 1.321 | 1.344 | 1.302 |
| 42 | 3.550 | 1.258 | 1.233 | 2.849 | 1.574 | 1.278 | 1.228 | 1.243 |
| 45 | 3.874 | 1.235 | 1.316 | 3.122 | 1.642 | 1.368 | 1.239 | 1.296 |
| 59 | 4.476 | 1.227 | 1.223 | 3.874 | 2.934 | 1.315 | 1.244 | 1.260 |
| 63 | 5.015 | 1.290 | 1.272 | 4.727 | 3.167 | 1.604 | 1.277 | 1.427 |
| 79 | 5.501 | 1.359 | 1.399 | 5.173 | 4.020 | 2.690 | 1.343 | 2.606 |

[1] 4-(2,6-dimethylheptyl) phenol

EXAMPLE 8

Example 5 was repeated with the exception that each sample contained 100 ppm of benzoyl peroxide initiator and 50 ppm of inhibitor. The viscosity data obtained are shown in Table 8.

Taking plots of the viscosity data compiled from Examples 5–8, induction times were estimated for these inhibitors. The induction time for the Control under each set of conditions in each Example was subtracted from the individual inhibitors to give a $\Delta t_i$ value which can be used as a measure of an inhibitor effectiveness. These data are shown in Table 9.

TABLE 8

VISCOSITIES OF SAMPLES IN CENTIPOISE
INHIBITORS

| Time hours | None, Control H | 4-t-Butyl Phenol | 4-sec-Butyl Phenol | 4-t-Butyl Catechol | Hydro-quinone | 4-Dodecyl Phenol | 4-n-Pentyl Phenol | 4-Nonyl Phenol[1] |
|---|---|---|---|---|---|---|---|---|
| 4 | 1.227 | 1.326 | 1.259 | 1.225 | 1.243 | 1.231 | 1.252 | 1.211 |
| 9 | 1.319 | 1.304 | 1.288 | 1.295 | 1.330 | 1.301 | 1.289 | 1.286 |
| 18.5 | 1.272 | 1.264 | 1.264 | 1.273 | 1.290 | 1.331 | 1.315 | 1.329 |
| 22.5 | 1.328 | 1.299 | 1.253 | 1.271 | 1.251 | 1.258 | 1.229 | 1.271 |
| 38.5 | 3.926 | 1.267 | 1.246 | 2.463 | 2.327 | 1.426 | 1.309 | 1.340 |
| 42.5 | 4.074 | 1.272 | 1.272 | 2.834 | 2.760 | 1.701 | 1.264 | 1.573 |
| 48.25 | 4.672 | 1.261 | 1.322 | 2.843 | 3.249 | 2.376 | 1.435 | 2.132 |
| 60 | 4.985 | 1.291 | 2.246 | 3.705 | 4.050 | 3.341 | 2.671 | 3.263 |
| 63 | 5.557 | 1.387 | 2.680 | 3.922 | 4.076 | 3.789 | 2.910 | 3.506 |
| 80 | 6.308 | 3.077 | 3.360 | 4.618 | 4.903 | 4.242 | 3.804 | 4.355 |

[1] 4-(2,6-dimethylheptyl) phenol

TABLE 9

INDUCTION PERIODS (Hrs.)

| | Inhibitor 25 ppm | | | | Inhibitor 50 ppm | | | | |
|---|---|---|---|---|---|---|---|---|---|
| | Initiator 100 ppm | | Initiator 0 ppm | | Initiator 100 ppm | | Initiator 0 ppm | | Total |
| Inhibitor | $t_i$ | $\Delta t_i$ | $t_i$ | $\Delta t_i$ | $t_i$ | $\Delta t_i$ | $t_i$ | $\Delta t_i$ | $\Sigma \Delta t_i$ |
| Control I | 25 | 0 | 27 | 0 | 25 | 0 | 25 | 0 | 0 |
| 4-t-Butyl Phenol | 36 | 11 | 44 | 17 | 63 | 38 | >80 | >55 | >121 |
| 4-sec-Butyl Phenol | 37 | 12 | 53 | 26 | 48 | 23 | >79 | >54 | >115 |
| 4-t-Butyl Catechol | 25 | 0 | 34 | 7 | 25 | 0 | 25 | 0 | 7 |
| Hydroquinone | 33 | 8 | 37 | 10 | 26 | 1 | 38 | 13 | 32 |
| 4-Dodecyl Phenol | 35 | 10 | 46 | 19 | 37 | 12 | 59 | 34 | 75 |
| 4-n-Pentyl Phenol | 37 | 12 | 50 | 23 | 41 | 16 | >80 | >55 | >106 |
| 4-Nonyl Phenol[1] | 25 | 0 | 48 | 21 | 38 | 13 | 58 | 33 | 67 |

*$t_i$ (of an inhibitor) = $t_i$ (of that inhibitor) − $t_i$ (control)

Although the invention has been described in its preferred forms with a certain degree of particularity, it is understood that the present disclosure of the preferred forms has been made only by way of example and that numerous changes may be resorted to without departing from the spirit and scope of the invention.

What is claimed is:

1. In the process for the production of vinyl acetate by the reaction of ethylene with molecular oxygen and acetic acid in the presence of a catalyst followed by a recovery of pure vinyl acetate from a crude reaction product by distillation, the improvement which comprises dissolving a p-alkyl phenol having 4 to 18 carbon atoms in the alkyl group in the crude product and maintaining a solution of p-alkyl phenol in the vinyl acetate through all distillation stages.

2. Process claimed in claim 1 wherein the p-alkyl phenol is 4-(2,6-dimethylheptyl) phenol.

3. Process claimed in claim 1 wherein the p-alkyl phenol is present in an amount ranging from 50 to 1000 parts per million based on the weight of vinyl acetate produced.

* * * * *